United States Patent [19]
Geissler et al.

[11] 4,031,156
[45] June 21, 1977

[54] SEPARATION AND RECOVERY OF ETHYLBENZENE BY DUAL DESORBENT COMPOSITION AND TEMPERATURE SEPARATION PROCESSES

[75] Inventors: Paul R. Geissler, Edison; Frank J. Healy, Morristown, both of N.J.

[73] Assignee: Exxon Research and Engineering Company, Linden, N.J.

[22] Filed: July 27, 1976

[21] Appl. No.: 708,924

Related U.S. Application Data

[63] Continuation-in-part of Ser. No. 556,435, March 7, 1975, abandoned.

[52] U.S. Cl. ............... 260/674 SA; 208/310 Z; 210/31 C
[51] Int. Cl.² ............... C07C 7/13; B01D 15/08; C10G 25/04
[58] Field of Search .......... 260/674 SA; 208/310 Z; 210/31 C

[56] References Cited

UNITED STATES PATENTS

| | | | |
|---|---|---|---|
| 3,201,491 | 8/1965 | Stine et al. | 260/676 MS |
| 3,455,815 | 7/1969 | Fickel | 208/310 |
| 3,696,107 | 10/1972 | Neuzil | 260/674 SA |
| 3,715,409 | 2/1973 | Broughton | 260/674 SA |
| 3,732,325 | 5/1973 | Pharis et al. | 260/674 SA |
| 3,761,533 | 9/1973 | Otani et al. | 260/674 SA |
| 3,843,518 | 10/1974 | Magee et al. | 210/31 C |
| 3,867,470 | 2/1975 | Van Grinsven et al. | 260/674 SA |

*Primary Examiner*—Delbert E. Gantz
*Assistant Examiner*—G. E. Schmitkons
*Attorney, Agent, or Firm*—C. Leon Kim

[57] ABSTRACT

Dual desorbent composition and/or dual temperature technique, when employed in a simulated moving-bed adsorption-desorption separation system embedded with a solid sorbent comprising certain sieves, e.g., Rb-exchanged Type X crystalline aluminosilicate sieve, which preferentially adsorb ethylbenzene, entails an improved separation and recovery of ethylbenzene from $C_8$ aromatic feedstreams as sorbate product. Further, certain specific sieves, which preferentially adsorb xylene isomers, i.e., orthoxylene, metaxylene and paraxylene, may also be employed, in said simulated process utilizing the dual desorbent composition and/or the dual temperature concept, in order to effect the improved separation and recovery of ethylbenzene from its $C_8$ aromatic isomers as raffinate product.

19 Claims, 3 Drawing Figures

Figure 1

DUAL DESORBENT COMPOSITION

Figure 2
DUAL TEMPERATURE

Figure 3

DUAL TEMPERATURE-COMPOSITION

SEPARATION AND RECOVERY OF ETHYLBENZENE BY DUAL DESORBENT COMPOSITION AND TEMPERATURE SEPARATION PROCESSES

CROSS REFERENCE TO RELATED APPLICATIONS

This application is a continuation-in-part of pending U.S. Ser. No. 556,435, filed Mar. 7, 1975, and now abandoned.

BACKGROUND OF THE INVENTION

This invention relates to the separation and recovery of ethylbenzene from $C_8$ aromatic isomer feedstreams in a simulated countercurrent flow system wherein a fluid stream containing said feedstream flows through serially and circularly interconnected desorption, rectification and adsorption zones. More particularly, it pertains to the use of certain specific sieves in combination with the dual desorbent composition technique which is carried out by employing two desorbent streams of different strengths to help minimize the total amount of desorbent requirements. Additionally, it concerns the use of said specific sieves and a temperature gradient technique which helps increase the strength of the desorbent employed.

The present process employing the above inventive concepts is an improvement of the simulated countercurrent flow processes described in U.S. Pat. No. 3,761,533 and U.S. Pat. No. 3,201,491. It is known that, in adsorption-separation processes of liquid feed mixtures, the technique of employing a moving-bed type adsorption process, wherein said moving bed comprises adsorbent particles which are counter-currently contacted with streams of liquid feedstock and desorbent, results in a high degree of purity for the adsorbed product. This process and the so-called simulated countercurrent flow system, wherein solid sorbent particles are stationary, have been proposed and disclosed in the above patents.

In the latter known process, an adsorption separation column is divided into three (or four equivalent) zones: a sorption zone, (a primary rectification zone,) a desorption zone and a (secondary) rectification zone. A downstream portion of the sorption zone is also called a primary rectification zone. Each of the three (or four) zones is divided into a plurality of serially interconnected sections, each section being packed with a mass of solid sorbent particles. In such a system, the separation is achieved by: introducing a desorbent stream into the first section of the desorption zone; introducing the liquid feed mixture to the first section of the sorption zone and withdrawing a raffinate effluent comprising a less sorbed component and the desorbent from the sorption zone. In order to maintain the simulated moving-bed operation, all the points of introducing and withdrawing the liquid streams into and from the sections are simultaneously shifted, at stated intervals of time, in a downstream direction, while maintaining the same order of continuity and the same spatial relationship between all the points.

In conducting the above-described process, several attempts were made to reduce the total desorbent requirements and also enhance the purity of the recovered sorbate. Stine et al., for example, disclosed a process in U.S. Pat. No. 3,201,491 (1965) which employs a portion of the desorption effluent withdrawn from the last section of the desorption zone by passing it directly into the (secondary) rectification zone in order to physically wash the raffinate materials remaining in the inactive void interstices between the active sorbent particles. An externally-prepared purging fluid comprising the sorbate and raffinate components of the feedstock was also claimed in their patent. Another improvement described in U.S. Pat. No. 3,455,815 (Fickel; 1967) and U.S. Pat. No. 3,696,107 (Neuzil; 1972) envisions the employment of a stream consisting essentially of an inert material in order to flush non-selectively sorbable components of the feedstock from the interstitial void spaces between the sorbent particles in the rectification zone. A third method of which is described in U.S. Pat. No. 3,761,533 (Otani et al.; 1973) introduces a portion of the desorption effluent which is rich in sorbate content into the rectification zone for the purpose of enhancing the purity of the sorbate component adsorbed within the rectification zone.

The above methods, however, contain certain deficiencies. The use of a portion of the desorption effluent will not only result in an increase in the desorbent consumption but also can desorb certain amount of sorbate adsorbed within the rectification zone and thereby limit the overall efficiency of the system. Further, Fickel's concept of employing a flushing stream consisting essentially of an inert material may not provide an adequate means to desorb chemically-adsorbed raffinate materials; and, consequently, the amount of desorbent requirements may not be lowered. It has now been discovered that the employment of the dual desorbent composition technique and/or the dual temperature technique described herein can substantially eliminate the above deficiencies and markedly improve the preferential separation of the ethylbenzene from $C_8$ aromatic isomer feedstreams.

SUMMARY OF THE INVENTION

In accordance with the present invention, simulated countercurrent flow adsorption-separation processes for the separation and recovery of ethylbenzene from $C_8$ aromatic isomer feedstreams are operated with the dual desorbent composition technique of the instant invention. In this inventive embodiment, two desorbent streams of different strengths are employed. The first desorbent stream, $D_1$, when employed in the desorption zone, is more strongly sorbable on the sorbent particles then the most strongly sorbable component of the feed stream, while the second desorbent stream, $D_2$, which is introduced into the rectification zone, is less sorbable than $D_1$ and is preferentially intermediate in strength between the most strongly adsorbed sorbate and the weakly adsorbed raffinate(s). $D_2$ may consist of the same desorbent material as $D_1$ but is made less strongly sorbable by dilution with an inert material such as a paraffin. The amount of the inert material employed in $D_2$ should not be higher than 85 weight percent of $D_2$.

In another separate embodiment of the present invention, the simulated countercurrent process can also be improved by the use of a temperature gradient technique. It has been discovered that, by preheating the desorbent stream to higher temperature prior to its introduction to the desorption zone with a heat exchanger or other suitable heating means, the desorbing strength of the desorbent stream can be significantly increased. In this embodiment, therefore, higher temperature in the desorption zone permit the use of smaller amounts of desorbent than would be required at lower temperatures. Simultaneously, in accordance with this embodiment, lower temperatures are employed in the rectification and the sorption zones to permit easy adsorption and rectification of the feed. In practicing this inventive embodiment, there should be maintained a minimum temperature difference of about 15° C. between the heated desorbent stream and the operating temperatures of the rectification and the sorption zones.

In a further embodiment, the simulated countercurrent flow separation process may be operated by combining both the dual desorbent composition and the dual temperature techniques. This embodiment utilizes a weaker desorbent $D_2$ in the rectification zone and a stronger desorbent $D_1$ in the desorption zone, with $D_1$ being at a higher temperature than $D_2$. The result of the combination would be a much greater saving in the desorbent requirements and in many cases result in greater reduction in cost than either of the embodiments effected separately.

In utilizing the novel concepts of this invention, the improved process is directed to the separation of ethylbenzene from $C_8$ aromatic isomer feedstream. The selective adsorption and separation of ethylbenzene from a $C_8$ aromatic isomer feedstream may be carried out by utilizing certain particular crystalline aluminosilicate sorbent materials which preferentially absorb ethylbenzene relative to other components of the feedstream such as orthoxylene, metaxylene and paraxylene.

It has been unexpectedly discovered that rubidium exchanged sodium Type X sieve preferentially adsorbs ethylbenzene and thereby efficiently separates same from $C_8$ aromatic isomer feedstreams. Another sieve found useful for separation of ethylbenzene in the above manner is cesium exchanged Type Y zeolite as disclosed in U.S. Pat. No. 3,626,020 (Neuzil; 1971). In a less preferred embodiment of the present invention, the separation of ethylbenzene from a $C_8$ aromatic isomer feedsteam may be carried out by utilizing certain sieve sorbent materials that selectively reject rather than adsorb ethylbenzene relative to the other components of the feedstream such as orthoxylene, metaxylene and paraxylene. In such cases the stronger desorbent ($D_1$) is then used to desorb more efficiently the more strongly adsorbed xylene isomers, resulting in a lower overall desorbent requirement for a given amount of $C_8$ aromatic feed. Sieves useful for this embodiment of the present invention includes sodium-Type Y, lithium-Type Y, calcium-Type Y, magnesium-Type Y and potassium exchanged steamed ammonium-Type Y sieves as taught in U.S. Pat. No. 3,686,343.

In this specification, carrier fluid or inert diluent is taken as liquid materials which are not significantly adsorbed by the sorbent substrate in the presence of feed mixture components. Eluent or desorbent is a term to describe liquid materials which are adsorbed by the substrate and compete for adsorption sites with the feed components.

The desorbent described above is generally a material capable of displacing sorbate component of the feedstock already adsorbed on the solid sorbent when the beds now comprising the desorption zone were in the rectification zone of a previous cycle of operation. The stream flowing through the successive beds of the desorption zone thus comprises a mixture of desorbent and desorbed sorbate released from an upstream bed of sorbent. Suitable desorbents useful in the present $C_8$ aromatic isomer separation process include toluene, m-diisopropylbenzene (m-DIPB), p-diethylbenzene (p-DEB), mixtures of diethylbenzene isomers (DEB), o-dichlorobenzene (o-DCB) and the like. While two different desorbent materials may be employed to prepare the stronger desorbent stream $D_1$, e.g., o-dichlorobenzene, and the weaker desorbent stream $D_2$, e.g., m-DIPB, it may be preferable to utilize one desorbent material admixed with different amounts of an inert material. Paraffinic materials having from 8 to 16 carbon atoms may be employed as the inert desorbent diluent. The stronger desorbent stream $D_1$ may be prepared by admixing, with an inert diluent, one of the desorbent materials enumerated above in an amount ranging from about 40 to about 100 wt. %, preferably from about 50 to about 95 wt. %, and more preferably from about 60 to about 85 wt. % based on the total amount of the desorbent mixture. Similarly, the weaker desorbent stream $D_2$ may comprise one of said desorbent materials in an amount within the range of from about 15 to about 60 weight percent, preferably from about 15 to about 50 weight percent, and more preferably from about 20 to about 35 weight percent based on the total mixture of the desorbent material and an inert diluent. The concentration of the desorbent material present in $D_1$ should be higher than that of the desorbent material present in $D_2$ at least by 20 wt. %. The volume ratio of the stronger desorbent stream $D_1$ to the weaker desorbent stream $D_2$ is in the range of from about 4/1 to about 1/3, preferably from about 3/1 to about 1/2, and more preferably from about 2/1 to about 1/1.

In applying the present invention to a commercial sorption-desorption system for separating $C_8$ aromatic isomers, the operating temperatures may vary from case to case. In general, however, the operable temperatures are in the range of from about 25° to about 200° C., preferably from about 75° to about 160° C., and more preferably from about 90° to about 145° C. When the dual temperature technique with a single desorbent stream is employed, the minimum temperature difference between the temperature of the desorbent stream introduced into the desorption zone and that of the streams flowing into the rectification and the sorption zones should be at least about 15° C. The upper limit of the temperature difference is normally controlled by the critical temperature at which $C_8$ aromatics begin to isomerize, e.g., about 200° C.

When this dual temperature technique with a single desorbent stream is employed, the desorbent stream may comprise one of the suitable desorbent materials enumerated above in an amount within the range of from about 15 to about 100 weight percent, preferably from about 20 to about 80 weight percent, and more preferably from about 25 to about 67 weight percent and the corresponding amounts of an inert material, e.g., $C_8$ to $C_{16}$ paraffinic materials.

DESCRIPTION OF THE PREFERRED EMBODIMENTS

Figure 1:
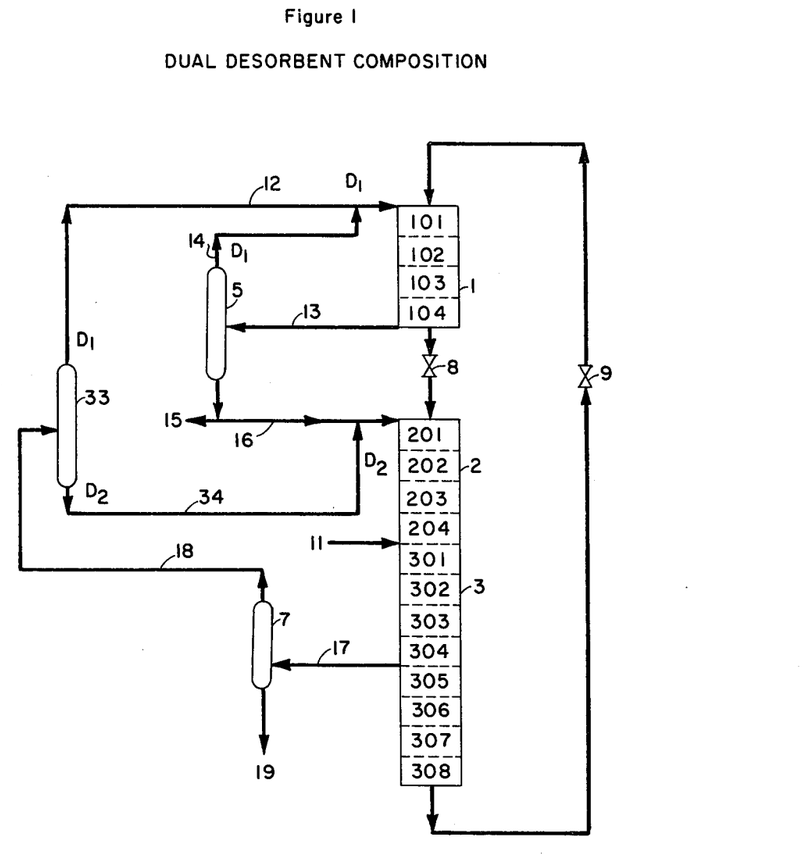
FIG. 1 represents a simplified version of a simulated moving-bed countercurrent separation system which employs two desorbent streams of different strengths: the stronger desorbent stream in the desorption zone and the weaker desorbent stream in the rectification zone.
Figure 2:
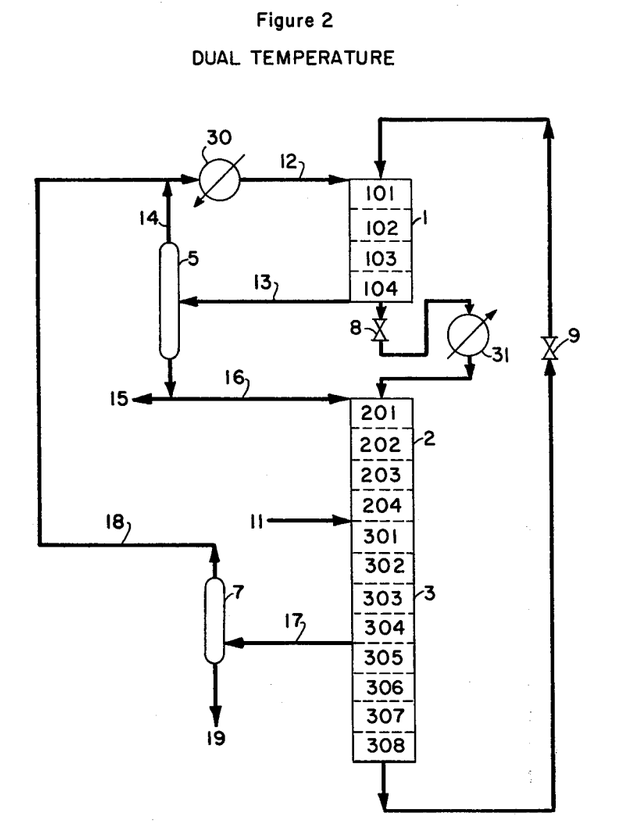
FIG. 2 shows a simulated moving-bed system which employs the desorbent stream with higher temperature in the desorption zone.
Figure 3:
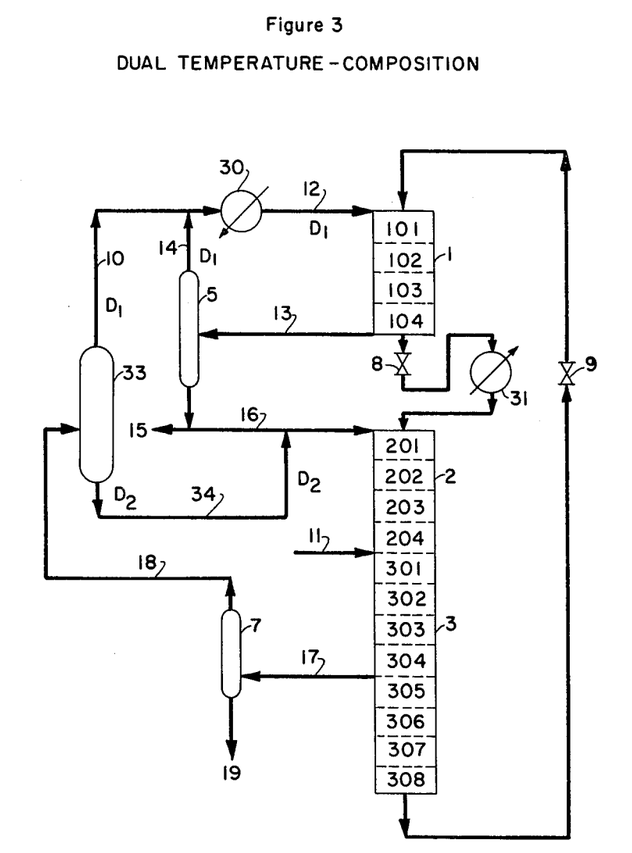
FIG. 3 illustrates a simulated moving-bed system which combines the dual desorbent composition and the dual temperature techniques in order to markedly enhance the separation efficiency of the system.

This instant invention and its embodiments will be further understood by reference to FIGS. 1, 2 and 3. The simulated moving-bed sorption-desorption systems illustrated in these figures are assumed to be under their steady-state operating conditions; and, consequently, it is assumed that no fresh feeds of the desorbent materials need be added as the desorbent streams with chosen concentrations will be constantly regenerated and recycled within the systems. As shown in FIG. 1, the stronger desorbent stream $D_1$ flows to the first section 101 of the desorption zone 1 through line 12 which is joined by line 14. It should be noted that this desorption zone, in the previous cycle of operation, functioned as the rectification zone 2; and that only the desired sorbate component, e.g., ethylbenzene, has been selectively retained in a high degree of purity, e.g., more than 90 weight %, and sorbed onto the solid sorbent particles charged in the desorption zone. This selectively retained sorbate is desorbed by the stronger desorbent stream 12 within the desorption zone 1; and the mixture comprising the eluted sorbate and the desorbent, which mixture will be called the desorption effluent, is withdrawn through an outlet of the last section 104 of the desorption zone 1. All or a major portion of this desorption effluent is then sent through line 13 to a distillation column 5 where the desorption effluent is separated into the desorbent stream 14 which is recycled to the desorption zone and the sorbate-product stream. All or a major portion of the sorbate product is withdrawn from the system as the final product 15; and the remaining minor portion 16 may be optionally sent to the top section 201 of the rectification zone 2 as a reflux stream. A minor portion of the desorption effluent may also be optionally routed to the rectification zone 2 through a valve 8. The weaker desorbent stream $D_2$ which is reconstituted in distillation column 33 is introduced, through line 34 joining line 16, into the top section 201 of the rectification zone 2 in order to effect the desorption of certain weakly-sorbed raffinates, e.g., metaxylene, orthoxylene and paraxylene, so that, when this rectification zone becomes a desorption zone in the future cycle of operation, only the desired sorbate component, e.g., ethylbenzene, may remain adsorbed on the sorbent substrate in a quality of high purity. A liquid feed mixture 11 comprising at least two sorbable $C_8$ aromatic isomers such as paraxylene, ethylbenzene, orthoxylene and metaxylene is injected into the top section 301 of the sorption zone 3. In the sorption zone 3, the feed flow joined by the effluent from the rectification zone (not shown) is countercurrently contacted with the simulated upward flow of the solid sorbent particles, resulting in the adsorption of the sorbable components of the feedstream onto the sorbent particles. The mixture of the desorbent and less sorbable raffinate materials which have lost sorption sites to more strongly sorbed molecules is then withdrawn from an outlet point positioned between sections 304 and 305 of the sorption zone 3 through line 17. This raffinate effluent is then sent to distillation column 7 wherein the raffinate effluent is separated into the desorbent stream 18 and the raffinate product 19.

In typical operations, the entire liquid stream flowing through the sorption zone 3 is divided into two portions: one portion being withdrawn from zone 3 as a raffinate effluent 17 and the other portion being allowed to flow directly down into the remaining sections 305, 306, 307, 308. These remaining sections are sometimes called a primary rectification zone. The number of the sections existing downstream from the withdrawal point of raffinate effluent 17 in the sorption zone 3 is determined in such a manner that the concentration of the raffinates contained in the stream flowing down through these sections reaches approximately zero at the bottom of the last section 308. Thus, the stream substantially free of raffinate components is directly and continuously introduced through a valve 9 into the desorption zone.

The sorption zone 3 may also be operated without the downstream sections 305, 306, 307 and 308. In this embodiment of operation, all or a major portion of the raffinate effluent 17 is withdrawn from the last section 304 of the sorption zone; and a minor portion of the raffinate effluent may be optionally routed, through valve 9, into the top section 101 of the desorption zone 1.

In general, the desorbent stream 18 recovered from distillation column 7 has a higher concentration than that of $D_2$, due to the influx of, in addition to the weaker desorbent stream $D_2$, an optional amount of the stronger desorbent stream $D_1$ from the desorption zone 1 through valve 8 into the rectification and the sorption zones 2,3 and also due to the presence of the strong desorbent material desorbed from the sorbent particles charged within the sortion zone 3. This strong desorbent material eluted in the sorption zone 3 is the fraction which has stayed adsorbed onto the sorbent substrate from the previous cycle when the sorption zone 3 functioned as the desorption zone 1. In order to reconstitute the weaker desorbent stream $D_2$, therefore, the desorbent stream 18 from distillation column 7 is further treated in distillation column 33. If two different desorbing materials or eluents are employed, the eluent with stronger desorbing ability can be recovered, for example, as the tops product and the weaker desorbing material as the bottoms product. If an identical desorbent material and a common diluent are used, the concentrations of the inert material in the bottoms and the tops product streams can be controlled so as to obtain the two $D_1$ and $D_2$ streams with their desired strengths.

The dual temperature embodiment may be more readily understood with reference to FIG. 2 which shows the desorbent stream being heated prior to its introduction to desorption zone 1 with a heat exchanger 30 or by other suitable means known in the art; and removing the residual heat, through the use of heat exchanger 31, before a portion of the desorption effluent passes into the rectification zone. Normally, the separation system is operated isothermally (except the desorption zone in this embodiment); and the temperature difference between the heated desorbent stream 12 and other streams going into the rectification zone should be maintained at least at about 15° C. It should be understood that the temperature of the reflux stream 16 has been adjusted, through the use of suitable means, e.g., a heat exchanger (not shown), so that the rectification zone can be maintained at a substantially isothermal condition. Flow sequence in FIG. 2 is otherwise identical to that described above for FIG. 1, except that distillation column 33 and associated stream 34 have been deleted.

Other applicable schemes for this embodiment include the utilization of distillation columns 5 and 7 in such a way to produce stream 12 at a sufficiently high temperature; and also heating of the desorption zone by means of a heating medium other than that desorbent stream, e.g., electric heating tapes, thereby eliminating the need for employing heat exchanger 30. Additionally, heat exchanger 31 may be eliminated if the heat capacity of desorption zone 1 is large enough to adequately cool the desorption effluent, a portion of which passing through valve 8.

The embodiment which combines both the dual temperature and the dual composition concepts may be more readily understood with reference to FIG. 3 which shows the strong desorbent stream (stream 10 from distillation column 33 and stream 14 from distillation column 5) being heated prior to its introduction to desorption zone 1 with a heat exchanger 30. Weak desorbent stream 34 flows into the first section 201 of the rectification zone 2, along with an optional amount of reflux stream 16. Stream 34 is weaker in desorbability than stream 12 by virtue of both its lower temperature and its lower concentration of eluent in its eluent-carrier or desorbent-diluent composition. Again, the temperatures of all the streams flowing into and leaving from the system, except the desorption zone in this embodiment, are assumed to be maintained substantially identical through the use of suitable means, e.g., a heat exchanger (not shown in FIG. 3), known in the art. Although it is not always necessary to maintain a minimum temperature difference between streams 12 and 34 in this embodiment, a higher temperature gradient is more desirable as it entails a higher efficiency. A minor portion of the desorption effluent from the last section 104 of the desorption zone may be optionally sent to the rectification zone after its temperature is adjusted to a temperature compatible to that of the rectification zone through the use of heat exchanger 31. Flow sequence in FIG. 3 is otherwise identical to that described above for FIG. 1.

The process of the present invention is further illustrated by the following examples.

EXAMPLE IA

This example is designed to show that a rubidium exchanged sodium Type X zeolite preferentially adsorbs ethylbenzene over other $C_8$ aromatic isomers.

A sodium Type X zeolite was first contacted with a 25% aqueous solution of rubidium chloride at about 50° C. for about 6 hours in order to effect a partial ion exchange between sodium and rubidium ions. This partially Rb-exchanged sodium Type X zeolite was then air calcined overnight, starting at room temperature and then at temperatures increased at the rate of 100° F. per hour until a final temperature of 1000° F. was reached, to yield a substantially dehydrated Type X zeolite sieve containing 6.7 wt. % Na and 1.05 wt. % Rb cation moieties.

Said dehydrated Na-Rb Type X zeolite sieve was contacted with a $C_8$ aromatic isomer mixture comprising 20% ethylbenzene, 20% paraxylene, 40% metaxylene and 20% orthoxylene until an equilibrium was reached. G.C. analysis showed that about 100 g. of said sieve would adsorb about 4.27 g. of ethylbenzene, 3.24 g. of paraxylene, 4.06 g. of metaxylene and 2.03 g. of orthoxylene.

EXAMPLE IB

This example is intended to demonstrate that in order to separate the ethylbenzene in a desired purity from the xylenes adsorbed on the Na-Rb Type X zeolite sieve prepared and tested in Example IA, the weak desorbent stream ($D_2$) should contain at least about 15 weight percent of an eluent, e.g., m-DIPB.

In order to obtain ethylbenzene as the sorbate product from the desorption zone in a relatively pure quality, e.g., (ethylbenzene/xylenes) 10, a major amount of the xylenes adsorbed in the adsorption zone should be desorbed in the rectification zone by employing the weak desorbent stream of a suitable strength. The maximum level of xylenes, denoted Z, which may remain adsorbed on the sorbent substrate when it is "moved upward" from the rectification zone to the desorption zone is thus determined as follows:

$$(\text{maximum } EB \text{ adsorbed}/Z) = \frac{4.27 \text{ g.}}{Z} = 10$$

$$\longrightarrow Z = 0.43 \text{ g.}$$

Accordingly, about 8.9 g. (= 9.33−0.43) of xylenes should be desorbed from said 100 g. of Na-Rb Type X zeolite sieve, described in Example IA, in the rectification zone. Assuming that the desorption would take place on an equimolar basis, the amount of eluent, e.g., m-DIPB, required to desorb said 8.9 g. of xylenes would be:

$$8.9 \text{ g.} \times \frac{162.28 \text{ (M.W. of m-DIPB)}}{106.15 \text{ (M.W. of xylenes)}} = 13.61 \text{ g.}$$

For the obvious economic consideration, however, only a limited amount of weak desorbent stream $D_2$ may be employed. For example, it is normally impractical to raise the weight ratio of $D_2$ to the xylenes desorbed in the rectification zone beyond 10. That is, $$\frac{D_2}{8.9} = \frac{(13.61 + \text{diluent})}{8.9} \leq 10$$

$$\longrightarrow \text{Max. amount of diluent} = 89 - 13.61 = 75.39 \text{ g.}$$

$$100 \times \frac{75.39}{89} = 84.7 \text{ wt. \%}$$

Examples IA and IB above show that high levels of xylene isomers as well as ethylbenzene are chemically adsorbed on the rubidium-exchanged sodium Type X zeolite; and that the weak desorbent stream should contain at least about 15 wt. % eluent in order to chemically desorb said xylene isomers in an economically feasible manner.

The following examples, being in the present tense, should be taken in conjunction with Examples IA and IB, as the best mode of carrying out the instant inventive embodiments; and not as reflecting an account of acts actually carried out by the applicants.

EXAMPLES 1 THROUGH 10

The process as shown in FIG. 1 utilizing distillation column 33 to supply a strong desorbent stream 12 and weak desorbent stream 34 is separately operated with various sieves at different temperatures. When a feed (stream 11) mixture composed of 20% ethylbenzene, 20% paraxylene, 40% metaxylene and 20% orthoxylene is used in the process, it is found that the volume ratios of desorbent to product are as shown in Table I.

EXAMPLES 11 THROUGH 20

The process as shown in FIG. 2 utilizing a heater 30 to preheat desorbent stream 12 to a temperature 30° C. higher than the desorbent temperature in section 201 is separately operated with the same sieves, temperatures, and the same feed mixture as in Examples 1 through 10. It is found that the volume ratios of desorbent to product are as shown in Table II.

EXAMPLES 21 THROUGH 30

The process as shown in FIG. 3 utilizing distillation column 33 and preheater 30 to supply a high temperature strong desorbent stream 12 and weak desorbent stream 34 at a temperature 30° lower than stream 12 is separately operated with the same sieves, temperature, and the same feed mixture as Examples 11 through 20. It is found that the volume ratios of desorbent to product are as shown in Table III.

EXAMPLES 31 THROUGH 40

The procedures of Examples 11 through 21 are separately repeated except that desorbent stream 12 is not heated and is at the same temperature as desorbent stream 34. It is found that the volume ratios of desorbent to product are as shown in Table IV.

Examples 1 through 40 show that the use of stronger desorbents in desorption zone 1, wherein its strength is increased by either an increase in temperature and/or an increase in eluent concentration, decreases the overall desorbent requirements and therefore results in a more efficient process for ethylbenzene separation and recovery.

TABLE I

| Example No. | Sieve | T° C. | Strong Desorbent[1] % Eluent | % Inert | Weak Desorbent[1] % Eluent | % Inert | Ratios[2][4] Desorbent Stream 14 / Product Stream 15 | | Desorbent Stream 18 / Raffinate Stream 19 | |
|---|---|---|---|---|---|---|---|---|---|---|
| 1 | NaY | 130 | 90% MDIPB | 10% Dodecane | 25% MDIPB | 75% Dodecane | 5 | (R) | 7 | (EB) |
| 2 | NaY | 130 | 75% MDIPB | 25% Dodecane | 33% MDIPB | 67% Dodecane | 6 | (R) | 6 | (EB) |
| 3 | LiY | 130 | 90% ODCB | 10% Dodecane | 30% ODCB | 70% Dodecane | 6 | (R) | 6 | (EB) |
| 4 | CaY | 80 | 90% T | 10% Hexane | 35% T | 65% Hexane | 6 | (R) | 7 | (EB) |
| 5 | CaY | 125 | 90% ODCB | 10% Dodecane | 25% ODCB | 75% Dodecane | 5 | (R) | 7 | (EB) |
| 6 | MgY | 120 | 80% DEB | 20% Dodecane | 30% DEB | 70% Dodecane | 6 | (R) | 6 | (EB) |
| 7 | RbX | 130 | 90% MDIPB | 10% Dodecane | 25% MDIPB | 75% Dodecane | 5 | (EB) | 6 | (R) |
| 8 | RbX | 130 | 85% DEB | 15% Dodecane | 20% DEB | 80% Dodecane | 5 | (EB) | 6 | (R) |
| 9[3] | KS+(NH$_3$)Y | 125 | 95% ODCB | 5% Dodecane | 25% ODCB | 75% Dodecane | 6 | (R) | 7 | (EB) |
| 10[3] | KS+(NH$_3$)Y | 125 | 90% DEB | 10% Dodecane | 30% DEB | 70% Dodecane | 5 | (R) | 7 | (EB) |

[1]MDIPB = metadiisopropylbenzene; ODCB = orthodichlorobenzene; DEB = diethylbenzene; T = toluene
[2]Product in Streams 15 and 19 identified in Table along with corresponding ratio EB = ethylbenzene, R = meta-, ortho- and paraxylene
[3]Sieve prepared according to U.S. Pat. No. 3,686,343
[4]The purity of the ethylbenzene recovered in each example is > 90 wt. %.

TABLE II

| Example No. | Sieve | T° C. | Desorbent[1] % Eluent | % Inert | Ratios[2][4] Desorbent Stream 14 / Product Stream 15 | | Desorbent Stream 18 / Raffinate Stream 19 | |
|---|---|---|---|---|---|---|---|---|
| 11 | NaY | 130 | 25% MDIPB | 75% Dodecane | 6 | (R) | 7 | (EB) |
| 12 | NaY | 130 | 33% MDIPB | 67% Dodecane | 7 | (R) | 6 | (EB) |
| 13 | LiY | 130 | 30% ODCB | 70% Dodecane | 6 | (R) | 6 | (EB) |
| 14 | CaY | 80 | 35% T | 65% Hexane | 7 | (R) | 7 | (EB) |
| 15 | CaY | 125 | 25% ODCB | 75% Dodecane | 6 | (R) | 7 | (EB) |
| 16 | MgY | 120 | 30% DEB | 70% Dodecane | 7 | (R) | 6 | (EB) |
| 17 | RbX | 130 | 25% MDIPB | 75% Dodecane | 8 | (EB) | 6 | (R) |
| 18 | RbX | 130 | 20% DEB | 80% Dodecane | 7 | (EB) | 6 | (R) |
| 19[3] | KS+(NH$_3$)Y | 125 | 25% ODCB | 75% Dodecane | 7 | (R) | 7 | (EB) |
| 20[3] | KS+(NH$_3$)Y | 125 | 30% DEB | 70% Dodecane | 7 | (R) | 7 | (EB) |

[1]MDIPB = metadiisopropylbenzene; ODCB = orthodichlorobenzene; DEB = diethylbenzene; T = toluene
[2]Product in Streams 15 and 19 identified in Table along with corresponding ratio EB = ethylbenzene R = meta-, ortho- and paraxylene
[3]Sieve prepared according to U.S. Pat. No. 3,686,343
[4]The purity of the ethylbenzene recovered in each example is > 90 wt. %.

TABLE III

| Example No. | Sieve | T° C. | Strong Desorbent[1] % Eluent | % Inert | Weak Desorbent[1] % Eluent | % Inert | Ratios[2][4] Desorbent Stream 14 / Product Stream 15 | | Desorbent Stream 18 / Raffinate Stream 19 | |
|---|---|---|---|---|---|---|---|---|---|---|
| 21 | NaY | 130 | 90% MDIPB | 10% Dodecane | 25% MDIPB | 75% Dodecane | 4 | (R) | 7 | (EB) |
| 22 | NaY | 130 | 75% MDIPB | 25% Dodecane | 33% MDIPB | 67% Dodecane | 5 | (R) | 6 | (EB) |
| 23 | LiY | 130 | 90% ODCB | 10% Dodecane | 30% ODCB | 70% Undecane | 5 | (R) | 6 | (EB) |
| 24 | CaY | 80 | 90% T | 10% Hexane | 35% T | 65% Hexane | 5 | (R) | 7 | (EB) |
| 25 | CaY | 125 | 90% ODCB | 10% Dodecane | 25% ODCB | 75% Dodecane | 4 | (R) | 7 | (EB) |
| 26 | MgY | 120 | 80% DEB | 20% Dodecane | 30% DEB | 70% Dodecane | 4 | (R) | 6 | (EB) |
| 27 | RbX | 130 | 90% MDIPB | 10% Dodecane | 25% MDIPB | 75% Dodecane | 4 | (EB) | 6 | (R) |

TABLE III-continued

| Example No. | Sieve | T° C. | Strong Desorbent[1] % Eluent | % Inert | Weak Desorbent[1] % Eluent | % Inert | Ratios[2×4] Desorbent Stream 14 Product Stream 15 | | Desorbent Stream 18 Raffinate Stream 19 | |
|---|---|---|---|---|---|---|---|---|---|---|
| 28 | RbX | 130 | 85% DEB | 15% Dodecane | 20% DEB | 80% Dodecane | 4 | (EB) | 6 | (R) |
| 29[3] | KS+(NH₃)Y | 125 | 95% ODCB | 5% Dodecane | 25% ODCB | 75% Dodecane | 5 | (R) | 7 | (EB) |
| 30[3] | KS+(NH₃)Y | 125 | 90% DEB | 10% Dodecane | 30% DEB | 70% Dodecane | 4 | (R) | 7 | (EB) |

[1]MDIPB = metadiisopropylbenzene; ODCB = orthodichlorobenzene; DEB = diethylbenzene; T = toluene
[2]Product in Streams 15 and 19 identified in Table along with corresponding ratio EB = ethylbenzene, R = meta-, ortho- and paraxylene
[3]Sieve prepared according to U.S. Pat. No. 3,686,343
[4]The purity of the ethylbenzene recovered in each example is > 90 wt. %.

TABLE IV

| Example No. | Sieve | T° C. | Desorbent[1] % Eluent | % Inert | Ratios[2×4] Desorbent Stream 14 Product Stream 15 | | Desorbent Stream 18 Raffinate Stream 19 | |
|---|---|---|---|---|---|---|---|---|
| 31 | NaY | 130 | 25% MDIPB | 75% Dodecane | 9 | (R) | 7 | (EB) |
| 32 | NaY | 130 | 33% MDIPB | 67% Dodecane | 10 | (R) | 6 | (EB) |
| 33 | LiY | 130 | 30% ODCB | 70% Dodecane | 9 | (R) | 6 | (EB) |
| 34 | CaY | 80 | 35% T | 65% Hexane | 11 | (R) | 7 | (EB) |
| 35 | CaY | 125 | 25% ODCB | 75% Dodecane | 9 | (R) | 7 | (EB) |
| 36 | MgY | 120 | 30% DEB | 70% Dodecane | 10 | (R) | 6 | (EB) |
| 37 | RbX | 130 | 25% MDIPB | 75% Dodecane | 10 | (EB) | 6 | (R) |
| 38 | RbX | 130 | 20% DEB | 80% Dodecane | 9 | (EB) | 6 | (R) |
| 39[3] | KS+(NH₃)Y | 125 | 25% ODCB | 75% Dodecane | 10 | (R) | 7 | (EB) |
| 40[3] | KS+(NH₃)Y | 125 | 30% DEB | 70% Dodecane | 9 | (R) | 7 | (EB) |

[1]MDIPB = metadiisopropylbenzene; ODCB = orthodichlorobenzene; DEB = diethylbenzene; T = toluene
[2]Product in Streams 15 and 19 identified in Table along with corresponding ration EB = ethylbenzene, R = meta-, ortho- and paraxylene
[3]Sieve prepared according to U.S. Pat. No. 3,686,343.
[4]The purity of the ethylbenzene recovered in each example is > 90 wt. %.

What is claimed is:

1. In a process for continuously separating, in a liquid phase, the components of a liquid $C_8$ aromatic feedstream containing ethylbenzene wherein at least one of said components is selectively adsorbed by contact with a solid sorbent material, utilizing a simulated countercurrent flow system wherein liquid streams are allowed to flow downward through a desorption zone, a rectification zone and a sorption zone, each zone being serially and circularly interconnected and divided into a plurality of serially interconnected sections, each section being packed with a mass of said solid sorbent material, the improvement which comprises:
   a. introducing a first desorbent stream containing a desorbent and a diluent into the first section of said desorption zone;
   b. withdrawing a desorption effluent containing a selectively sorbed component from the last section of said desorption zone;
   c. introducing a second desorbent stream containing said diluent and at least about 15 weight percent of said desorbent into the first section of said rectification zone;
   d. introducing said hydrocarbon feedstream into the first section of said sorption zone;
   e. withdrawing a raffinate effluent containing a less sorbed component from the last section of said sorption zone; and
   f. wherein the concentration of said desorbent present in the first desorbent stream is higher than the concentration of said desorbent present in the second desorbent stream by at least 20 weight percent.

2. The process of claim 1 wherein the first desorbent stream employed in step (a) is heated, before it is introduced into the first section of said desorption zone, to a temperature higher than the temperature of the second desorbent stream employed in step (c).

3. The process of claim 1 wherein said diluent is a $C_8$ to $C_{16}$ paraffin.

4. The process of claim 1 wherein said desorbent is selected from the group consisting of toluene, m-diisopropylbenzene, p-diethylbenzene, o-dichlorobenzene and a mixture of diethylbenzene isomers.

5. The process of claim 1 wherein said sorbent material is a crystalline aluminosilicate selected from the group consisting of rubidium-exchanged sodium Type X and cesium-exchanged Type Y sieves.

6. The process of claim 5 wherein said selectively sorbed component withdrawn in step (b) is ethylbenzene.

7. The process of claim 5 wherein said less sorbed component withdrawn in step (c) is a xylene isomer.

8. The process of claim 1 wherein said sorbent material is a crystalline aluminosilicate selected from the group consisting of sodium Type Y, lithium Type Y, calcium Type Y, magnesium Type Y and potassium-exchanged steamed ammonium Type Y sieves.

9. The process of claim 8 wherein said selectively sorbed component withdrawn in step (b) is a xylene isomer.

10. The process of claim 9 wherein said less sorbed component withdrawn in step (c) is ethylbenzene.

11. In a process for continuously separating, in a liquid phase, the components of a liquid $C_8$ aromatic feedstream containing a xylene isomer and ethylbenzene wherein at least one of said components is selectively adsorbed by contact with a solid sorbent material, utilizing a simulated countercurrent flow system wherein liquid streams are allowed to flow downward through a desorption zone, a rectification zone and a sorption zone, each zone being serially and circularly interconnected and divided into a plurality of serially interconnected sections, each section being packed with a mass of said solid sorbent material, the improvement which comprises:
  a. introducing, into the first section of said desorption zone, a first desorbent stream comprising a desorbent selected from the group consisting of m-diisopropylbenzene, toluene, p-diethylbenzene, o-dichlorobenzene and a mixture of diethylbenzene isomers in an amount ranging from about 40 to about 100 weight percent and a paraffinic diluent having from 8 to 16 carbon atoms;
  b. withdrawing a desorption effluent containing ethylbenzene from the last section of said desorption zone;
  c. introducing, into the first section of said rectification zone, a second desorbent stream containing said paraffinic diluent and from about 15 to about 60 weight percent of said desorbent;
  b. introducing said hydrocarbon feedstream into the first section of said sorption zone;
  e. withdrawing a raffinate effluent containing said xylene isomer from the last section of said sorption zone; and
  f. wherein the concentration of said desorbent present in the first desorbent stream is higher than the concentration of said desorbent present in the second desorbent stream by at least 20 weight percent.

12. The process of claim 11 wherein the first desorbent stream employed in step (a) is heated, before it is introduced into the first section of said desorption zone, to a temperature higher than the temperature of the second desorbent stream employed in step (c).

13. The process of claim 11 wherein said xylene isomer is selected from the group consisting of orthoxylene, metaxylene and paraxylene.

14. The process of claim 11 wherein said sorbent material is a crystalline aluminosilicate selected from the group consisting of rubidium-exchanged sodium Type X and cesium-exchanged Type Y sieves.

15. The process of claim 14 wherein said sorbent material is rubidium-exchanged sodium Type X zeolite sieve.

16. In a process for continuously separating, in a liquid phase, the components of a liquid $C_8$ aromatic feedstream containing a xylene isomer and ethylbenzene wherein at least one of said components is selectively adsorbed by contact with a solid sorbent material, utilizing a simulated countercurrent flow system wherein liquid streams are allowed to flow downward through a desorption zone, a rectification zone and a sorption zone, each zone being serially and circularly interconnected and divided into a plurality of serially interconnected sections, each station being packed with a mass of said solid sorbent materials, the improvement which comprises:
  a. introducing, into the first section of said desorption zone, a first desorbent stream comprising a desorbent selected from the group consisting of m-diisopropylbenzene, toluene, p-diethylbenzene, o-dichlorobenzene and a mixture of diethylbenzene isomers in an amount ranging from about 40 to about 100 weight percent and a paraffinic diluent having from 8 to 16 carbon atoms;
  b. withdrawing a desorption effluent containing said xylene isomer from the last section of said desorption zone;
  c. introducing, into the first section of said rectification zone, a second desorbent stream containing said paraffinic diluent and from about 15 to about 60 weight percent of said desorbent;
  d. introducing said hydrocarbon feedstream into the first section of said sorption zone;
  e. withdrawing a raffinate effluent containing ethylbenzene from the last section of said sorption zone; and
  f. wherein the concentration of said desorbent present in the first desorbent stream is higher than the concentration of said desorbent present in the second desorbent stream by at least 20 weight percent.

17. The process of claim 16 wherein the first desorbent stream employed in step (a) is heated, before it is introduced into the first section of said desorption zone, to a temperature higher than the temperature of the second desorbent stream employed in step (c).

18. The process of claim 16 wherein said sorbent material is a crystalline aluminosilicate selected from the group consisting of sodium Type Y, lithium Type Y, calcium Type Y, magnesium Type Y and potassium-exchanged steamed ammonium Type Y sieves.

19. The process of claim 16 wherein said xylene isomer is selected from the group consisting of orthoxylene, metaxylene and paraxylene.

* * * * *